United States Patent [19]
Edwards et al.

[11] Patent Number: 6,114,394
[45] Date of Patent: Sep. 5, 2000

[54] POLYAMINE DERIVATIVES AS RADIOPROTECTIVE AGENTS

[75] Inventors: Michael L. Edwards, Cincinnati; Ronald D. Snyder, Loveland, both of Ohio

[73] Assignee: Merrell Pharmaceuticals Inc., Bridgewater, N.J.

[21] Appl. No.: 08/949,536

[22] Filed: Oct. 14, 1997

Related U.S. Application Data

[63] Continuation of application No. 08/507,368, filed as application No. PCT/US94/01128, Aug. 22, 1995, abandoned, which is a continuation of application No. 08/021,363, Feb. 23, 1993, abandoned.

[51] Int. Cl.$^7$ .................... A61K 31/135; C07C 211/00
[52] U.S. Cl. .................. 514/646; 514/579; 514/654; 514/655; 514/657; 564/305; 564/384; 564/387
[58] Field of Search ..................... 514/579, 646, 514/657, 655, 654; 564/512, 646, 654, 305, 384, 387

[56] References Cited

U.S. PATENT DOCUMENTS

| | | |
|---|---|---|
| 2,653,977 | 9/1953 | Craig et al. |
| 2,951,092 | 8/1960 | Sowinski et al. |
| 3,369,905 | 2/1968 | Jones et al. |
| 3,892,824 | 7/1975 | Piper et al. ............... 260/944 |
| 4,591,605 | 5/1986 | Ray ........................ 514/579 |
| 5,109,024 | 4/1992 | Prakash et al. |
| 5,217,964 | 6/1993 | Edwards et al. |
| 5,342,945 | 8/1994 | Bergeron ................. 544/296 |

FOREIGN PATENT DOCUMENTS

| | | |
|---|---|---|
| 0311068 | 4/1984 | European Pat. Off. |
| 0277635 | 8/1988 | European Pat. Off. |
| 0308757 | 3/1989 | European Pat. Off. |
| 0311068 | 4/1989 | European Pat. Off. |
| 0349224 | 1/1990 | European Pat. Off. |
| 0 378 146 | 7/1990 | European Pat. Off. |
| 0378146 | 7/1990 | European Pat. Off. |
| 0495450 | 7/1992 | European Pat. Off. |
| 0497202 | 8/1992 | European Pat. Off. |
| 15318 | 4/1971 | Japan |
| 37020 | 4/1971 | Japan |
| 46-15318 | 4/1971 | Japan |
| 9205142 | 4/1992 | WIPO |
| 9302045 | 4/1993 | WIPO |
| 9317689 | 9/1993 | WIPO |
| 9419311 | 9/1994 | WIPO |

OTHER PUBLICATIONS

Edwards et al., "Polyamine analogues with antitumor activity." J. Med. Chem., vol. 33, pp. 1369–1375, 1990.
He et al., Eur. J. Biochem. vol. 221, pp. 391–398, 1994.
Rehse et al., Arch. Pharm. (Weinheim), vol. 323, pp. 287–294, 1990.
Snyder et al., Biochem. Biophys. Res. Commun., vol. 176, pp. 1383–1382, 1991.
Dalheim et al., Radiobiologiya, vol. 29(3), pp. 338–342, 1989.
Rehse et al., Arch. Pharm. (Weinheim) vol. 323, pp. 287–294, 1990.
Held et al., Int. J. Radiat. Biol., vol. 59(3), pp. 699–710, 1991.
Moroz et al., Probl. Gematol. Pereliv. Krovi, vol. 27(8), pp. 49–51, 1982.
Rehse et al., "Antiaggregatorische und anticoagulante Eigenschaften von Oligoaminen, 12. Mitt.: Alkyl–und Arylalkylderivate von Putrescin, Spermindin und Spermin." Archiv der Pharmazie, vol. 323 (5): 287–294, 1990.
Piper, James R. et al., The J. of Organic Chemistry, vol. 33, No. 2, pp 636–642 (1968).
Edwards, et al., J of Medicinal Chem 33(5):1369–1375 (1990).
Edwards, et al., J of Medicinal Chem. 34(2):569–574 (1991).
Edwards, et al., J of Medicinal Chem 34(8):2414–2420 (1991).
Israel, et al., J. Med. Chem. 7:710–716 (1964).
Jakus J. et al., The Jour. of Biological Chemistry, vol. 268, No. 18, pp. 13151–13159 (1993).
Piper, James R. et al., The J. of Organic Chem. vol. 33, No. 2, pp. 636–642 (1968).
Rehse, Klaus et al., Arch. Pharm. (Weinheim) 323 (5), 287–294, 1990.
He, et al., Eur. J. Biochem., 221(1), 391–398 (1994).
Jakus, et al., J. Biol. Chem., 268(18), 1351–1359 (1993).
Edwards, et al., J. of Medicinal Chem 34(2):569–74 (1991).
Israel, et al., J. Med. Chem. 7:710716 (Nov. 1964).
Rehse, et al., Arch. Pharm (Weinheim), vol. 323, No. 5, pp 287–294 (1990).
Jakus J. et al., J. of Biological Chemistry, vol. 268, No. 18, pp. 13151–13159 (1993).

*Primary Examiner*—Barbara Badio
*Attorney, Agent, or Firm*—Balaram Gupta

[57] ABSTRACT

The present invention relates to polyamine derivatives of the formula $RHN-(CH_2)_m-NH-(CH_2)_n-NHR$ wherein m is an integer from 2 to 4, n is an integer from 3 to 10 and R is $C_2-C_6$ alkyl or $—(CH_2)_p-Ar$ wherein Ar is phenyl or naphthyl and p is an integer from 0 to 2; and the pharmaceutically acceptable addition salts thereof which are useful as radioprotective agents. It relates also to the use of polyamines of the formula $RHN-(CH_2)_m-NH-(CH_2)_n-NH-(CH_2)_m-NHR$ wherein m is an integer from 2 to 4, n is an integer from 3 to 10 and R is $C_2-C_6$ alkyl or $—(CH_2)_p-Ar$ wherein Ar is phenyl or naphthyl and p is an integer from 0 to 2; and the pharmaceutically acceptable addition salts thereof as radioprotective agents.

15 Claims, No Drawings

POLYAMINE DERIVATIVES AS RADIOPROTECTIVE AGENTS

CROSS-REFERENCE TO RELATED APPLICATION

This is a continuation of application Ser. No. 08/507,368, filed Jul. 5, 1996, now abandoned which has an effective international filing date of Jan. 31, 1994 as application PCT/US94/01128 which designated the U.S. and entered the U.S. national phase on Aug. 22, 1995 under 35 USC 371 and was assigned Ser. No. 08/507,368, which is a continuation of application Ser. No. 08/021,363, filed Feb. 23, 1993, now abandoned, which are herein incorporated by reference.

BACKGROUND OF THE INVENTION

Radioprotective agents, also known as radioprotectors, are defined as agents which protect cells or organisms from deleterious cellular effects of exposure to ionizing radiation. These deleterious cellular effects include damage to cellular DNA, such as DNA strand break, disruption in cellular function, cell death, tumor induction and the like. The mechanism of this protective effect may at least partially be due to radical scavenging properties of the radioprotective agents.

The potential utility of these agents in protecting against exposure to environmental radiation, as well as in cancer radiation therapy, has long bee recognized. These agents, administered prior to or during exposure, would eliminate or reduce the severity of deleterious cellular effects caused by exposure to environmental ionizing radiation such as resulting from a nuclear explosion, a spill of radioactive material, close proximity to radioactive material and the like.

In addition, these agents are believed to provide a selective protection of normal cells, and not of cancer cells, during cancer radiation therapy. For example, these agents, administered to the cancer patient prior to or during radiation therapy, will be absorbed by normal, non-cancer cells to provide a protective effect. However, the radioprotective agents will not be absorbed to the same extent by tumor cells due to the poor vascularity associated with the tumor. Therefore, the radioprotective agents would provide a selective protective effect on the normal cells as compared to tumor cells and would eliminate or reduce the severity of deleterious cellular effects of radiation therapy on normal cells. Furthermore, some radioprotective agents may act as prodrugs and require activation by cellular enzymatic processes which are not fully operative in the cancer cell. These agents, even if absorbed in a similar concentration in normal and cancer cells, will only be activated in cells with normal enzymatic processes and not in cancer cells. These prodrug radioprotective agents would be activated to provide a selective protective effect only in normal cells and would thus eliminate or reduce the severity of deleterious cellular effects of radiation therapy on normal cells.

Furthermore, certain radioprotective agents provide a selective protection against deleterious cellular effects in normal cells caused by certain DNA-reactive agents such as cisplatin, cyclophosphamide, diethylnitrosoamine, benzo(a) pyrene, carboplatin, doxorubicin, mitomycin-C and the like. Many of these DNA-reactive agents are chemotherapeutic agents useful in cancer therapy. Radioprotective agents are useful in eliminating or reducing the severity of deleterious effects in normal cells caused by exposure to these DNA-reactive agents, such as during cancer therapy with DNA-reactive chemotherapeutic agents.

In addition, certain radioprotective agents provide a selective protection against therapy-induced secondary tumor induction [See Grdina et al., *Pharmac. Ther.* 39, 21(1988)]. Radiation and chemotherapy provide effective treatments for a variety of neoplastic disease states. Unfortunately, these treatments themselves are oftentimes mutagenic and/or carcinogenic and result in therapy-induced secondary tumor induction. For example, patients treated for Hodgkin's disease appear to exhibit a relatively high risk for therapy-induced acute myelogenous leukemia and non-Hodgkin's lymphoma. Radioprotective agents provide selective protection against deleterious cellular effects, such as tumor induction, caused by radiation therapy or chemotherapy with a DNA-reactive chemotherapeutic agent. Radioprotective agents are thus useful in eliminating or reducing the risk of secondary tumor induction brought about by radiotherapy or chemotherapy.

Radioprotective agents thus are useful in eliminating or reducing the severity of deleterious cellular effects in normal cells caused by environmental exposure to ionizing radiation, cancer radiation therapy and treatment with DNA-reactive chemotherapeutic agents. See generally, Weiss and Simic, *Pharmac. Ther.* 39, 1 (1988).

The prototypical radioprotective agent, developed by the Antiradiation Drug Development Program at the Walter Reed Army Institute of Research, is WR-2721, or S-2(3-aminopropylamino)ethylphosphorothioic acid, which has the structure

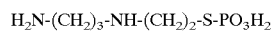  WR-2721.

Other known radioprotective agents are WR-1065, thought to be a metabolite, of WR-2721, which has the structure

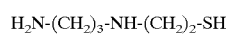  WR-1065, and WR-151,327, which has the structure

  WR-151,327.

SUMMARY OF THE INVENTION

The present invention provides a method of protecting mammalian cells from deleterious cellular effects caused by exposure to ionizing radiation or to a DNA-reactive agent comprising contacting said cells with a protective amount of a compound of formula (I)

  (I)

wherein
  m is an integer from 2 to 4
  n is an integer from 4 to 10 and
  R is $C_2$–$C_6$ alkyl or —$(CH_2)_p$-AR
wherein
  Ar is phenyl or naphthyl and
  p is an integer from 0 to 2;
and the pharmaceutically acceptable addition salts thereof.

The present invention further relates to compounds having the following formula (II)

  (II)

wherein
  m is an integer from 2 to 4 n is an integer from 3 to 10 and
R is $C_2$–$C_6$ alkyl or —$(CH_2)_p$-Ar
wherein
Ar is phenyl or naphthyl and
p is an integer from 0 to 2;
and the pharmaceutically acceptable addition salts thereof.

The present invention further provides a method of protecting mammalian cells from deleterious cellular effects caused by exposure to ionizing radiation or to a DNA-reactive agent comprising contacting said cells with a protective amount of a compound of formula (II).

The present invention also provides a method of protecting non-cancer cells of a human from deleterious cellular effects caused by exposure to ionizing radiation or by exposure to a DNA-reactive agent comprising administering to said human a protective amount of a compound of formula (I) or (II).

The present invention further provides a method of treating a patient in need of radiation therapy, or in need of chemotherapy with a DNA-reactive chemotherapeutic agent, comprising administering to said patient a protective amount of a compound of formula (I) or (II).

DETAILED DESCRIPTION OF THE INVENTION

As used herein, the following terms have the meanings as indicated below:

(1) the term "$C_2$–$C_6$" refers to a saturated straight or branched chain hydrocarbyl radical or two to six carbon atoms. Included within the scope of this term are ethyl, n-propyl, isopropyl, n-butyl, isobutyl, sec-butyl, t-butyl, n-pentyl, n-hexyl and the like.

2) The term "Ts" refers to a tosylate functionality of the formula:

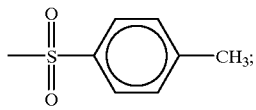

3) The term "Ph" refers to a phenyl functionality of the formula:

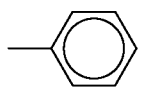

4) The term "Et" refers to an ethyl functionality of the formula:

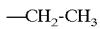

5) The term "Pr" refers to a propyl functionality of the formula:

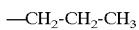

6) The term "Bu" refers to a butyl functionality of the formula:

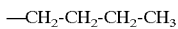

9) The term "pharmaceutically acceptable addition salts" is intended to apply to any non-toxic organic or inorganic acid addition salt of the base compounds represented by Formula (I) or (II). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methanesulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

Polyamine derivatives of formula (I) can be prepared as described in European Patent Application Publication No. 0 277 635, published Aug. 10, 1988 and in European Patent Application Publication No. 0 311 068, published Apr. 12, 1989. The choice of any specific route of preparation is dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (I).

The following reaction schemes are illustrative of the pathways by which the compounds of formula (I) may be made.

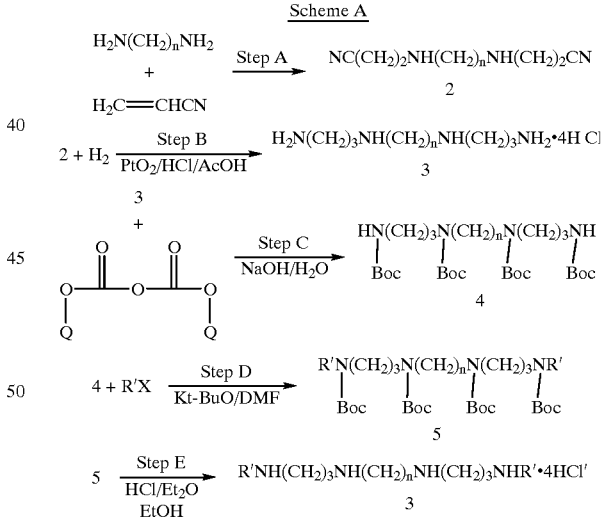

R' is defined as R in formula (I) except that when R is —$(CH_2)_p$-Ar, p cannot be zero. Boc is the t-butoxycarbonyl protecting group, Q is t-butyl and X is bromide, chloride or iodide.

In the foregoing five step process the initial step entails a specific N-alkylation designed to produce compounds wherein m is 3 and which entails the reaction of a diamine (wherein n is as generally defined in formula (I)) with 2 equivalents of acrylonitrile by heating reactants, either in a suitable solvent or neat, according to standard conditions well known in the art. The resulting cyano derivatives (2) are chemically reduced by reaction with hydrogen in the presence of a catalyst ($PtO_2$) in a suitable solvent with 8 equivalents of hydrochloric or hydrobromic acid to produce the resulting hydrohalic salts according to standard procedures well known in the art. Other reducing systems may also be utilized such as reduction with lithium aluminum hydride to produce compounds of structure (3). These compounds are then neutralized with base and the nitrogen atoms are protected, with di-t-butyldicarbonate according to standard operating conditions. The tetra N-protected amines (4) are alkylated with the appropriate alkyl halide by reaction in the presence of potassium butoxide according to standard alkylation procedures. Following alkylation the N-protective groups are removed by standard procedures, such as treatment with acid, preferably hydrochloric acid, in the presence of a suitable solvent or solvent system, such as diethyloxide in ethanol, to provide the desired products (6).

Alternatively compounds of structure (3) may be subjected to a reductive alkylation using an appropriate aldehyde; the reduction being effected by hydrogenation in the presence of $PtO_2$ according to well known procedures. This procedure does not require protection of the nitrogen atoms of the intermediates.

Scheme B describes the preparation of compounds of formula (I) wherein m is four (but can also be applicable where m is 2 to 4) and are otherwise analogous to those compounds identified as (6) in Scheme A.

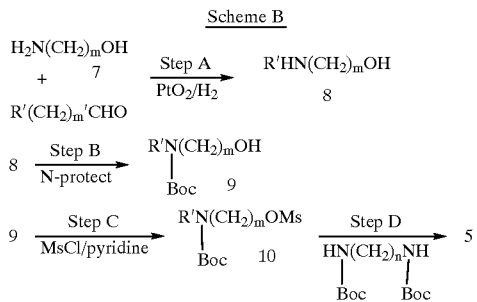

Ms is methanesulfonyl, m' is zero or a positive integer, and R' is defined as in scheme A. This reaction is initiated by reductive alkylation techniques using an amino alcohol (7) and an appropriate aldehyde to form R' substituted amino alcohols (8) which are N-protected. The N-protected amino alcohols (9) are converted to their mesylates (10) by standard reaction conditions, such as reacting with methanesulfonyl chloride in the presence of pyridine, preferably in the presence of a solvent such as methylene chloride.

The mesylate is subjected to alkylation with an N-protected diamine, such as $BocNH(CH_2)_nNHBoc$ using potassium t-butoxide in a suitable solvent, such as dimethylformamide using standard procedure. The so-produced tetra N-protected tetramines (5) are deprotected as in Scheme A. In essence the foregoing reductive alkylation, N-protection, mesylation, alkylation and deprotection procedures all employ techniques and reaction conditions which are well known in the art.

Scheme C describes an alternative method to prepare compounds of formula (I) wherein m is 2 to prepare intermediates (13) which are subjected to the alkylation procedures described in Scheme A.

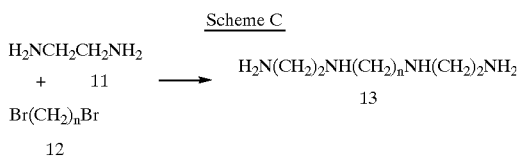

The foregoing N-alkylation entails the reaction of an appropriate dihaloalkane (12) with excess quantities (10X) of ethylene diamine (11) by heating the reactants at reflux in a suitable solvent, such as ethanol. Preparation of the desired final products bearing the R substituents on the terminal nitrogen atoms of intermediate (13) may be effected by N-protecting the intermediates (13) alkylating and deprotecting by methods analogous to steps C, D and E of Scheme A.

An alternative method for preparing compounds wherein Ar represents phenethyl or naphthylethyl is the reaction of an aroyl chloride as described in Scheme D.

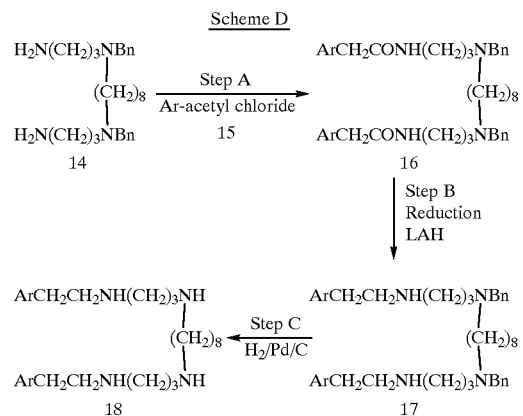

LAH is lithium aluminum hydride and Bn is benzyl. As described in Scheme D, the partially protected intermediate (14) is N-alkylated with an arylacetyl chloride (15), such as phenylacetyl chloride in the presence of triethylamine, using an inert solvent, to form the amide (16). The amide (16) is then chemically reduced, preferably with lithium aluminum hydride and the resulting product (17) is catalytically de-benzylated using hydrogen over palladium on carbon to provide the desired compound described by structure (18). These steps entail reaction techniques and procedures well known and understood in the art.

In those instances wherein Ar represents an aromatic moiety (phenyl or naphthyl) and p is zero such that Ar is attached directly to the terminal nitrogen atoms, then such compounds may be prepared according to the general sequence depicted in Scheme E.

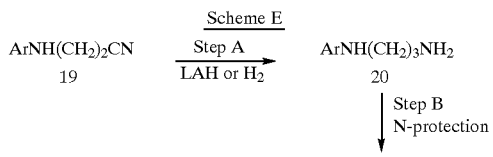

-continued

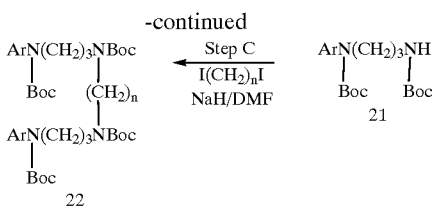

The foregoing reaction scheme depicts the preparation of compounds wherein Ar is phenyl, the first step of which is a lithium aluminum hydride reduction effected according to procedures published in the art (Bull. Soc. Chim. Fr., Part 2, 165–7(1979). Of course this reaction scheme can be expanded to include naphthyl. The N-protection employs t-butoxycarbonyl protecting groups which are put on and taken off according to standard techniques described previously. The N-protected compounds are alkylated by reaction with an appropriate dihalo alkane using standard and well known procedures. Deprotection of (22) by techniques well known in the art provides the desired compounds formula (I) wherein R is Ar and p is zero.

Alternatively compounds of formula (I) may be prepared by the method described in Scheme F.

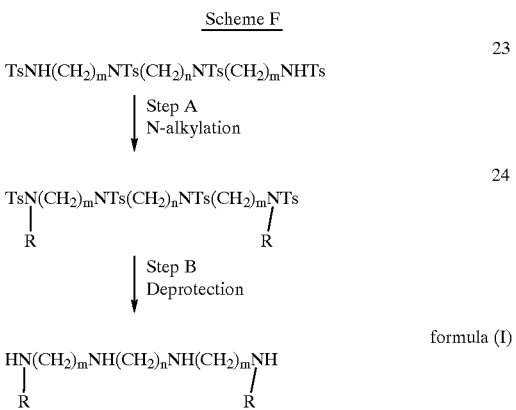

The compounds of structure (23) are readily available to one of ordinary skill in the art and can be prepared generally as described in European Patent Application No. 0 349 224, published Mar. 1, 1990. The tetra N-tosylated amine of structure (23) is alkylated to provide the di-N-alkylated compound described by structure (24).

For example, in step A, the tetra N-tosylated amine (23) can be treated with 2 equivalents of a suitable base, such as sodium hydride in a suitable solvent, such as dimethylformamide and then subsequently treated with 2 equivalents of the appropriately substituted alkyl halide to provide the di-N-alkylated product described by structure (24).

Alternatively in step A, the tetra N-tosylated amine (23) can be alkylated under Mitsunobu conditions. For example compound (23) can be treated with 3 equivalents of triphenylphosphine in a suitable organic solvent, such as tetrahydrofuran. This is then treated with 3 equivalents of an appropriate alkyl alcohol, such as ethanol followed by treatment with 3 equivalents of diethyl azodicarboxylate to afford the di-N-alkylated product described by structure (24).

The di-N-alkylated compound described by structure (24) is then deprotected by techniques well known in the art to provide the desired product of formula (I).

For example compound (24) can be treated with 48% aqueous hydrogen bromide under an atmosphere of nitrogen and heated to approximately 100° C. for about 20 hours to provide the desired product of formula (I) as the tetra hydrobromide salt.

In order to illustrate the preparation of the polyamine derivatives of formula (I), the following examples are provided. The reagents and starting materials are readily available to one of ordinary skill in the art. These examples are illustrative only and are not intended to limit the invention in any way. As used in the following examples, the following terms have the meanings indicated: "eq." refers to equivalents, "g" refers to grams, "mg" refers to milligrams, "mmol" refers to millimoles, "mL" refers to milliliters, "° C." refers to degrees Celsius, "TLC" refers to thin layer chromatography, "$R_f$" refers to retention factor and "δ" refers to parts per million down field from tetramethylsilane.

EXAMPLE 1

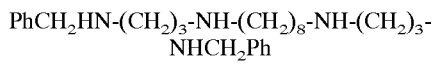

Preparation of N,N'-Bis-(3-benzylamino-propyl)-octane-1, 8-diamine·4HCL.

Scheme A, step A; Dissolve 1,8 diaminooctane (28.8 g, 0.2 mol) in ethanol (250 mL). Add acrylonitrile (27 mL, 0.41 mol) and gently reflux the mixture overnight. Remove the solvent under reduced pressure to provide N,N'-bis-[2-(cyano)ethyl]-1,8-diamino-octane.

Scheme A, step B; Combine N,N'-bis-[2,2'-bis(cyano) ethyl]-1,8-diamino-octane (50 g) with $PtO_2$ (2.0 g) in concentrated hydrochloric acid (133 mL). Place in a shaker flask at 45 lbs./sq. in. until hydrogen is no longer taken up. Filter the mixture and remove the solvent under vacuum. Triturate the residue with ethanol (1 L). Collect the product by filtration and dry the product to provide 1,5,14,18-tetraazaoctadecane tetrahydrochloride (51.6 g), $R_f$=0.17 eluting with 40% $NH_3$/methanol.

Scheme A, step C; Treat 1,5,14,18-tetraazaoctadecane tetrahydrochloride (28 g, 0.069 mol) with sodium hydroxide (10.99 g, 0.274 mol) in water (120 mL). When the reaction becomes homogenous add di-t-butylcarbonate (65.7 g, 0.307 mol) in tetrahydrofuran (750 mL) and stir for 16 hours. Separate the layers and extract the aqueous layer with methylene chloride (2×500 mL). Combine the organic extracts and organic layer, dry over anhydrous magnesium sulfate, filter and concentrate under vacuum. Purify the residue by flash chromatography (25% ethyl acetate/hexane, silica gel) to provide 1,5,14,18-tetra(t-butoxycarbonyl)-1,5, 14,18-tetraazaoctadecane (30.2 g), $R_f$=0.33 eluting with 25% ethyl acetate/hexane.

Scheme A, step D; Dissolve 1,5,14,18-tetra(t-butoxycarbonyl)-1,5,14,18-tetraazaoctadecane (20.0 g, 0.03 mol) in dimethylformamide (30 mL). Treat the solution with potassium t-butoxide (7.5 g, 0.067 mol) and benzyl bromide (7.96 mL, 0.067 mol) and stir for 18 hours. Concentrate the reaction under vacuum (0.5 mm at 45° C.). Dissolve the reside in ethyl acetate (1.4 L) and rinse with water (2×500 mL). Dry the organic layer over anhydrous magnesium sulfate, filter and concentrate under vacuum. Purify the residue by flash chromatography (20% ethyl acetate/hexane, silica gel) to provide 1,18-bis[(phenyl)methyl]-1,5,14,18-tetra(t-butoxycarbonyl)-1,5,14,18-tetraazaoctadecane (12.4 g) $R_f$=0.42 eluting with 25% ethyl acetate/hexane.

Scheme A, step E; Dissolve 1,18-bis[(phenyl)methyl]-1, 5,14,18-tetra(t-butyoxycarbonyl)-1,5,14,18-tetraazaoctadecane (12.4 g, 0.0147 mol) in anhydrous ethanol (14.7 mL) and treat with 2N hydrochloric acid in diethyl ether (160 mL). Stir the reaction overnight. Filter the reaction and rinse the filtrate with diethyl ether to provide the title compound (7.2 g) after drying, $R_f$=0.24 eluting with 10% conc. $NH_3$/methanol mp 311–312° C. (dec.).

EXAMPLE 2

BuHN-(CH$_2$)$_3$-NH-(CH$_2$)$_8$-NH-(CH$_2$)$_3$-NHBu

Preparation of N,N'-Bis-(3-butylamino-propyl)-octane-1,8-diamine·4HCL.

Scheme A, step D; Combine 1,5,14,18-tetra(t-butoxycarbonyl)-1,5,14,18-tetraazaoctadecane (3.5 g, 0.0053 mol), prepared as in step C or example 1, with potassium t-butoxide (2.7 g, 0.024 mol) and 1-iodobutane (2.57 mL, 0.024 mol) in dimethylformamide (10 mL). Stir the reaction for 18 hours. Concentrate the reaction under vacuum (0.5 mm at 45° C.) and dissolve the residue in ethyl acetate (500 mL). Wash with water (2×100 mL), dry over anhydrous magnesium sulfate, filter and concentrate under vacuum. Purify the residue by flash chromatography (20% ethyl acetate/hexane, silica gel) to provide 1,18-bis-(butyl)-1,5,14,18-tetra(t-butoxycarbonyl)-1,5,14,18-tetraazaoctadecane (1.32 g), $R_f$=0.36 eluting with 20% ethyl acetate/hexane.

Scheme A, step E; Dissolve 1,18-bis-(butyl)-1,5,14,18-tetra(t-butoxycarbonyl)-1,5,14,18-tetraazaoctadecane (1.32 g, 0.0017 mol) in anhydrous ethanol (1.7 mL) and treat with 2N hydrochloric acid in diethyl ether (17 mL). Stir the reaction overnight. Filter and wash the precipitate with diethyl ether. Recrystallize the product from isopropanol/water to provide the title compound (0.62 g) after drying under vacuum (0.1 mm) over $P_2O_5$ at 79° C., $R_f$=0.47 eluting with 20% conc $NH_3$/methanol, mp 320–322° C. (dec.).

EXAMPLE 3

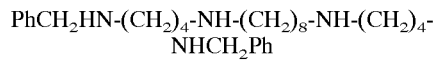
PhCH$_2$HN-(CH$_2$)$_4$-NH-(CH$_2$)$_8$-NH-(CH$_2$)$_4$-NHCH$_2$Ph

Preparation of N,N'-Bis-(4-benzylamino-butyl)-octane-1,8-diamine·4HCL.

Scheme B, step A; Dissolve diaminooctane (10.8 g, 0.075) in methylene chloride (200 mL), methanol (100 mL) with di-t-butyldicarbonate (32.7 g, 0.156 mol). Stir the reaction overnight. Concentrate the reaction under vacuum and crystallize the residue from hexane to provide N,N'-bis(t-butoxycarbonyl)-1,8-octanediamine (20.2 g), mp 96–97° C. Combine 4-amino-butan-1-ol (8.9 g, 0.1 mol), benzaldehyde (10.6 g, 0.1 mol), ethanol (100 mL) and $PtO_2$ (0.3 g) and hydrogenate at 45 lbs./sq. in. until hydrogen is no longer taken up. Filter the reaction and concentrate the filtrate under vacuum to provide 4-[[(phenyl)methyl]amino]-butan-1-ol (17.7 g), $R_f$=0.70 eluting with 10% conc. $NH_3$/methanol.

Scheme B, step B; Combine [[(phenyl)methyl]amino]-butan-1-ol (17.7 g, 0.1 mol) and di-t-butyldicarbonate (31.8 g, 0.15 mol) in methylene chloride (100 mL) and stir overnight. Concentrate the reaction under vacuum and purify the residue by flash chromatography (25% ethyl acetate/hexane, silica gel) to provide 4-[N-(t-butoxycarbonyl)-N-[(phenyl)methyl]-amino]butan-1-ol, $R_f$=0.27 eluting with 20% ethyl acetate/hexane.

Scheme B, step C; Cool a mixture of 4-[N-(t-butoxycarbonyl)-N-[(phenyl)methyl]-amino]butan-1-ol (21.8 g, 0.078 mol), methylene chloride (250 mL) and pyridine (9.7 mL). Add mesylchloride (6.65 mL, 0.086 mol) in methylene chloride (6.6 mL) dropwise to the reaction with stirring. After addition is complete, allow the reaction to warm to room temperature and stir for an additional 2 hours. Pour the reaction into methylene chloride (200 mL), rinse with 0.5 N hydrochloric acid (500 mL), saturated sodium bicarbonate (500 mL), dry over anhydrous magnesium sulfate, filter and concentrate under vacuum. Purify the residue by flash chromatography (25% ethyl acetate/hexane, silica gel) to provide 4-[N-(t-butoxycarbonyl)-N-[(phenyl)methyl]-amino]-1-methansulfonyl butane (10.7 g), $R_f$=0.36 eluting with 25% ethyl acetate/hexane.

Scheme B, step D; Combine N,N'-bis(t-butoxycarbonyl)-1,8-octanediamine (5.16 g, 0.015 mol) from step A and 4-[N-(t-butoxycarbonyl)-N-[(phenyl)methyl]-amino]-1methansulfonyl butane (10.7 g, 0.032 mol) from step D with potassium t-butoxide (3.92 g), sodium iodide (0.2 g) and dimethylformamide (60 mL). Stir the reaction for 72 hours and concentrate under vacuum. Dissolve the residue in ethyl acetate (600 mL) and rinse with water (200 mL). Dry the organic layer over anhydrous magnesium sulfate, filter and concentrate under vacuum. Purify the residue by flash chromatography (20% ethyl acetate/hexane, silica gel) to provide 1,20-bis[(phenyl)methyl]-1,16,15,20-tetra-(t-butoxycarbonyl)-1,6,15,20-tetraazaeicosane, $R_f$=0.22 eluting with 20% ethyl acetate/hexane.

Scheme A, step E; Dissolve 1,20-bis[(phenyl)methyl]-1,16,15,20-tetra-(t-butoxycarbonyl)-1,6,15,20-tetraazaeicosane (4.7 g, 0.0054 mol) in ethanol (5 mL) and treat with 2N hydrochloric acid in diethyl ether (54 mL). Stir the reaction overnight. Filter the reaction, collect and recrystallize the precipitate from isopropanol/water to provide the title compound, $R_f$=0.47 eluting with 10% conc $NH_3$/methanol, mp 319–321° C.

EXAMPLE 4

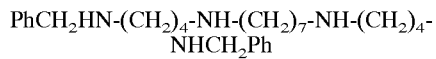
PhCH$_2$HN-(CH$_2$)$_4$-NH-(CH$_2$)$_7$-NH-(CH$_2$)$_4$-NHCH$_2$Ph

Preparation of N,N'-Bis-(4-benzylamino-butyl)-heptane-1,7-diamine·4HCl.

The title compound can be prepared in a manner analogous to that described in example 3, utilizing 1,7-diaminoheptane in step A, mp 327–328° C. (dec.).

EXAMPLE 5

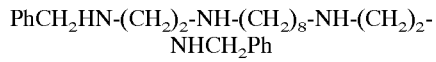
PhCH$_2$HN-(CH$_2$)$_2$-NH-(CH$_2$)$_8$-NH-(CH$_2$)$_2$-NHCH$_2$Ph

Preparation of N,N'-Bis-(2-benzylamino-ethyl)-octane-1,8-diamine·4HCL.

Scheme C; Combine 1,8-dibromooctane (4.75 g, 0.017 mol) with ethanol (20 mL) and ethylene diamine (9.32 mL). Reflux the reaction overnight. After cooling, treat the reaction with sodium hydroxide (1.4 g) and concentrate under vacuum. Triturate the residue with methylene chloride (2×200 mL) and filter. Treat the filtrate with di-t-butyldicarbonate (66.6 g) and stir overnight. Concentrate the reaction under vacuum and purify the residue by flash chromatography (25% ethyl acetate/hexane, silica gel) to provide 1,4,13,16-tetra(t-butoxycarbonyl)-1,4,13,16-tetraazahexadecane, $R_f$=0.64 elution with 50% ethyl acetate/hexane. This product may then prepared in a manner analogous to steps D and E of example 1 to provide the title compound, mp 306.5–308.5° C. (dec.).

EXAMPLE 6

PhCH$_2$HN-(CH$_2$)$_2$-NH-(CH$_2$)$_7$-NH-(CH$_2$)$_2$-NHCH$_2$Ph

Preparation of N,N'-Bis-(2-benzylamino-ethyl)-heptane-1,7-diamine·4HCl.

The title compound can be prepared in a manner analogous to example 5 utilizing 1,7-dibromoheptane and ethylene diamine, mp 314–315° C. (dec.).

EXAMPLE 7

Preparation of N,N'-Bis-(2benzylamino-ethyl)-decane-1,10-diamine·4HCl.

The title compound can be prepared in a manner analogous to example 5 utilizing 1,10-dibromodecane and ethylene diamine, mp 332–323° C. (dec.).

EXAMPLE 8

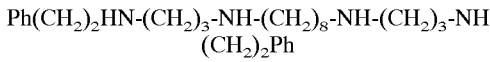

Preparation of N,N'-Bis-(3phenethylamino-propyl)-octane-1,8-diamine·4HCl.

Scheme D, Step A; Cool a solution of 5,14-bis[(phenyl)methyl]-1,5,14,18-tetraazaoctadecane (2.2 g, 5 mmol) and triethylamine (2 g, 20 mmol) in chloroform (100 mL) in an ice bath. Add a solution of phenylacetyl chloride (2.3 g, 15 mmol) in chloroform (10 mL) dropwise. Allow the reaction to warm to room temperature and stir for 18 hours. Rinse the reaction with aqueous sodium bicarbonate, dry the organic layer over anhydrous magnesium sulfate, filter and concentrate under vacuum. Purify the residue by flash chromatography (ethyl acetate, silica gel) to provide 1,18-bis[[(phenyl)methyl]carbonyl]-5,14-bis-[(phenyl)methyl]-1,5,14,18-tetraazaoctadecane (3 g) as a thick oil.

Scheme D, step B; Add a solution of 1,18-bis[[(phenyl)methyl]carbonyl]-5,14-bis-[(phenyl)methyl]-1,5,14,18-tetraazaoctadecane (3 g) in tetrahydrofuran (150 mL) dropwise to a suspension of lithium aluminum hydride (0.5 g) in tetrahydrofuran (500 mL). Stir the reaction for 48 hours at room temperature. Decompose the excess reducing agent by dropwise addition of water (1 mL), 15% sodium hydroxide (1 mL) and water (3 mL). Filter the mixture and concentrate the filtrate under vacuum. Dissolve the residue in ethanol (100 mL) and add anhydrous hydrogen chloride gas to provide the tetrahydrochloride salt of 1,18-bis[(2-phenyl)ethyl]-5,14-bis-[(phenyl)methyl]-1,5,14,18-tetraazaoctadecane. Scheme D, step C: Hydrogenate this product in ethanol (150 mL) in the presence of Pearlman's catalyst (0.3 g) at 43 psig on a Parr hydrogenation apparatus for 24 hours. Filter the reaction and concentrate the filtrate under vacuum. Crystallize the residue from 2-propanol to provide the title compound as a hemihydrate, mp 322–324° C. (dec.).

EXAMPLE 9

Preparation of N,N'-Bis-(3-benzylamino-propyl)-butane-1,4-diamine·4HCl.

Combine spermine (2.02 g), benzaldehyde (2.13 mL), ethanol (40 mL) and PtO$_2$ (0.1 g) and treat with hydrogen at 45 lbs./sq. in. until hydrogen is no longer taken up. Remove the catalyst by filtration, add 1N hydrochloric acid (100 mL), add water until the solids dissolve and then add isopropanol until the solution becomes turbid. Cool, filter and collect the solid to provide the title compound (2.0 g) after drying, R$_f$=0.50 eluting with 20% conc. NH$_3$/methanol, mp 328–329° C. (dec.).

EXAMPLE 10

Preparation of N,N'-Bis-(3-benzylamino-propyl)-heptane-1,7-diamine·4HCl.

The title compound can be prepared in a manner analogous to that described in example 1, utilizing 1,7-dibromoheptane in step A, mp 319–320° C. (dec.).

EXAMPLE 11

Preparation of N,N'-Bis-(3-benzylamino-propyl)-nonane-1,9-diamine·4HCl.

The title compound can be prepared in a manner analogous to that described in example 1, utilizing 1,7-dibromononane in step A, mp 319–319.5° C. (dec.).

EXAMPLE 12

Preparation of N,N'-Bis-(3-benzylamino-propyl)-decane-1,10-diamine·4HCl.

The title compound can be prepared in a manner analogous to that described in example 1, utilizing 1,7-dibromodecane in step A, mp 318–319° C. (dec.).

EXAMPLE 13

Preparation of N,N'-Bis-(3-ethylamino-propyl)-heptane-1,7-diamine·4HCl.

The title compound can be prepared in a manner analogous to that described in example 2, utilizing 1,7-dibromoheptane in the sequence from example 1, step A and iodoethane example 2, step A, mp 322–323° C.

EXAMPLE 14

Preparation of N,N'-Bis-(3-propylamino-propyl)-heptane-1,7-diamine·4HCl.

The title compound can be prepared in a manner analogous to that described in example 2, utilizing 1,7-dibromoheptane in the sequence from example 1, step A and 1-iodopropane example 2, step A, mp 334–335° C.

EXAMPLE 14a

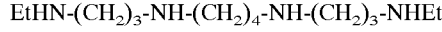

Preparation of N,N'-Bis-(3-ethylamino-propyl)-butane-1,4-diamine·4HBr.

Scheme F; Add spermine·4HCl (4.5 g, 13 mmol) to 10% sodium hydroxide (200 mL) and cool to 0° C. At 0° C. add a solution of tosyl chloride (52.3 mmol) in methylene chloride (200 mL) dropwise, allow the reaction to warm to room temperature and stir for 2 days. Separate the layers and extract the organic with 1N hydrochloric acid. Dry the organic layer over anhydrous magnesium sulfate, filter and concentrate under vacuum to provide the tetra N-tosylate tetra-amine (10.8 g) as a white foam.

Scheme F, step A; Dissolve the above prepared tetra N-tosylate tetra-amine (10.8 g, 13.2 mmol) in tetrahydrofuran (300 mL), add triphenylphosphine (10.3 g, 39 mmol) and ethanol (1.8 g, 39 mmol). Add dropwise a solution of diethyl azodicarboxylate (6.9 g, 39 mmol) in tetrahydrofuran (8 mL) and stir for 18 hours. Concentrate the reaction under vacuum and purify the residue by flash chromatography (silica gel, 10% ethyl acetate/toluene to provide the protected di-N-alkylated tetra-amine (4.0 g).

Scheme F, step B; Add aqueous 48% hydrogen bromide (250 mL) to the above protected di-N-alkylated tetra-amine (4.0 g) and heat to 100° C. under an atmosphere of nitrogen for 20 hours. After cooling concentrate the reaction under vacuum. Add ethanol and reconcentrate under vacuum. Recrystallize the residue form ethanol/water to yield the tetra-hydrobromide salt of the title compound (2 g) as a white solid, mp 309–310° C.

The polyamine derivatives of formula (II) can be prepared utilizing techniques well known in the art. The choice of any specific route of preparation is dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (II).

The following reaction schemes are illustrative of the pathways by which the compounds of formula (II) may be made. The reagents and starting materials are readily available to one of ordinary skill in the art. The polyamine derivatives of formula (II) can be prepared as described in Scheme G wherein m is 3, n is 3 to 10 and R' is defined as R in formula (II) except that when R is —(CH$_2$)$_p$-Ar, p cannot be zero. All other substituents, unless otherwise indicated, are previously defined.

reduction in step B to the triamine of structure (27). In step C the triamine of structure (27) is protected as the tri-tosylate by methods well known in the art and generally described in European Patent Application No. 0 349 224, published Mar. 1, 1990.

The tri-N-tosylated triamine is then alkylated to provide the tri-tosylated di-N-alkylated triamine described by structure (29).

For example,, in step D the tri-N-tosylated triamine (28) can be treated with 2 equivalents of a suitable base, such as sodium hydride in a suitable solvent, such as dimethylformamide and then subsequently treated with 2 equivalents of the appropriately substituted alkyl halide to provide the tri-tosylated di-N-alkylated product described by structure (29).

Alternatively in step D, the tri-N-tosylated triamine (28) can be alkylated under Mitsunobu conditions. For example compound (28) is treated with 3 equivalents of triphenylphosphine in a suitable organic solvent, such as tetrahydrofuran. This is then treated with 3 equivalents of an appropriate alkyl alcohol, such as ethanol followed by treatment with 3 equivalents of diethyl azodicarboxylate to afford the tri-tosylated di-N-alkylated product described by structure (29).

The tri-tosylated di-N-alkylated compound described by structure (29) is then deprotected by techniques well known in the art to provide the desired product of structure (30).

For example, in step E the tri-tosylated di-N-alkylated compound described by structure (29) can be treated with 48% aqueous hydrogen bromide under an atmosphere of nitrogen and heated to approximately 100° C. for about 20 hours to provide the desired product of structure (30) as the tetra hydrobromide salt.

The polyamine derivatives of formula (II) can be prepared as described in Scheme H wherein m' is 2 or 4, n is 3 to 10 and R' is defined as R in formula (II) except that when R is —(CH$_2$)$_p$—Ar, p cannot be zero. All other substituents, unless otherwise indicated, are previously defined. The reagents and starting materials are readily available to one of ordinary skill in the art.

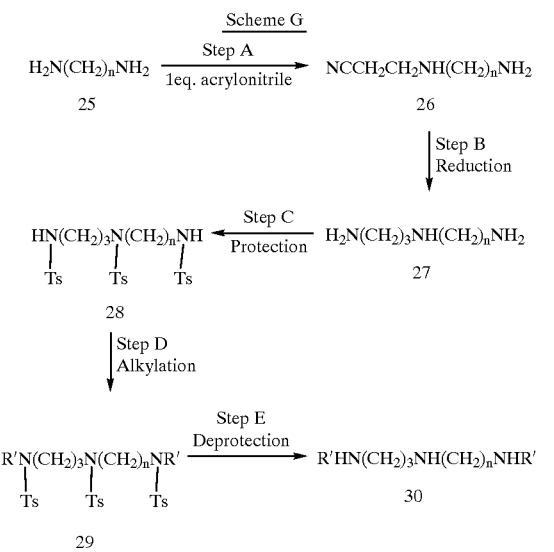

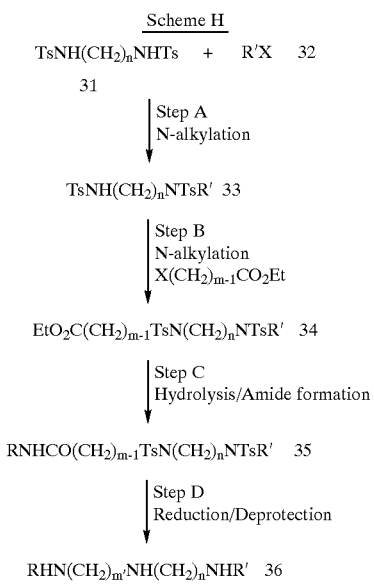

The compounds described by structure (27) can be prepared in a manner analogous to step A and step B of scheme A from the appropriately substituted diamine of structure (25) by treatment with one equivalent of acrylonitrile in step A to provide the nitrile of structure (26) and subsequent In scheme H, step A the appropriately substituted di-N-tosylated diamine (31) [prepared generally following the procedure disclosed in European Patent Application No. 0

349 224 published Mar. 1, 1990] is mono-N-alkylated to provide the mono-N-alkylated diamine of structure (33).

For example, the appropriately substituted di-N-tosylated diamine (31) is dissolved in a suitable solvent, such as tetrahydrofuran and treated with one equivalent of a suitable base, such as sodium hydride. The reaction is allowed to stir for approximately 30 minutes and one equivalent of an appropriately substituted alkyl halide is added. The reaction is heated to about 30° C. to 67° C. for about 1 to 24 hours. The desired mono-N-alkylated diamine (33) is then isolated by extractive techniques well known in the art.

In step B, the mono-N-alkylated diamine (33) is then alkylated with the appropriately substituted ethyl haloacetate or ethyl 4-halobutyrate to provide di-N-alkylated diamine described by structure (34).

For example, the mono-N-alkylated diamine (33) is dissolved in a suitable solvent, such as tetrahydrofuran and treated with one equivalent of a suitable base, such as sodium hydride. The reaction is allowed to stir for approximately 30 minutes and one equivalent of the appropriately substituted ethyl haloacetate or ethyl 4-halobutyrate is added. Examples of an appropriately substituted ethyl haloacetate or ethyl 4-halobutyrate are ethyl chloroacetate, ethyl bromoacetate, ethyl 4-chloroacetate and ethyl 4-bromoacetate. The reaction is then heated to about 30° C. to 67° C. for about 1 to 24 hours. The desired di-N-alkylated diamine (34) is then isolated by techniques well known in the art.

In step C, the ester of the di-N-alkylated diamine (34) is then hydrolyzed under basic conditions and the resulting acid is subsequently coupled to a primary amine using standard peptide formation techniques well known in the art to provide the appropriately substituted amide described by structure (35).

For example, the ester of the di-N-alkylated diamine (34) is dissolved in a suitable solvent, such as ethanol and treated with an excess of a suitable base, such as potassium hydroxide. The reaction is allowed to stir at about 25° C. to 50° C. for about 0.5 to 24 hours. The resulting potassium salt is collected by filtration and treated directly with 2.2 equivalents of oxalyl chloride as described in the alternative procedure below. Alternatively the resulting potassium salt is neutralized with a suitable aqueous acid, such as 2N hydrochloric acid and the acid product isolated by extractive methods well known in the art. The acid is then coupled to a suitable amine of formula RNH$_2$ following the procedure described directly below.

For example, the above formed acid of the di-N-alkylated diamine (34) is combined with 1.1 equivalents hydroxybenztriazole, 1.1 equivalents of 1-(3-dimethylaminopropyl)-3-ethyl carbodiimide hydrochloride and 1 equivalent of an appropriately substituted primary amine, such as benzyl amine. A solution of 2.2 equivalents of diisopropylethylamine in methylene chloride is added and the reaction is stirred at room temperature for 1 to 6 hours. The product is then isolated by techniques well known in the art. For example the reaction is diluted with ethyl acetate, washed with cold 0.5N hydrochloric acid, saturated sodium bicarbonate, brine, dried over anhydrous sodium sulfate, filtered and concentrated under vacuum to provide the appropriately substituted amide described by structure (35).

Alternatively, the acid of the di-N-alkylated diamine (34) may be dissolved in a suitable solvent, such as toluene and treated with 1.1 equivalents of thionyl chloride and allowed to stir for 1 to 5 hours at a temperature of about 25° C. to 40° C. The solvent is then removed under vacuum, the residue dissolved in a suitable solvent such as tetrahydrofuran and 1 equivalent of an appropriately substituted primary amine, such as benzyl amine is added. The reaction is stirred for about 1 to 24 hours and the product is then isolated by extractive methods well known in the art to provide the appropriately substituted amide described by structure (35). Alternatively if the potassium salt is utilized, the above procedure is followed substituting 2.2 equivalents of oxalyl chloride for 1.1 equivalents of thionyl chloride.

In step D the appropriately substituted amide (35) is then reduced to the desired triamine described by structure (36).

For example, appropriately substituted amide (35) is dissolved in a suitable solvent, such as 1,2-dimethoxyethane and treated with an excess of lithium aluminum hydride. The reaction is heated to about 40° C. to 85° C. for about 3 to 24 hours. After cooling, the product is isolated by techniques well known in the art to provide the desired triamine (36) wherein m' is 2 or 4, n is 3 to 10 and R' is defined as R in formula (II) except that when R is —(CH$_2$)$_p$—Ar, p cannot be zero.

An alternative method for the preparation of compounds of formula (II) is described in scheme I wherein all substituents, unless otherwise indicated, are previously defined. The reagents and starting materials are readily available to one of ordinary skill in the art Scheme I

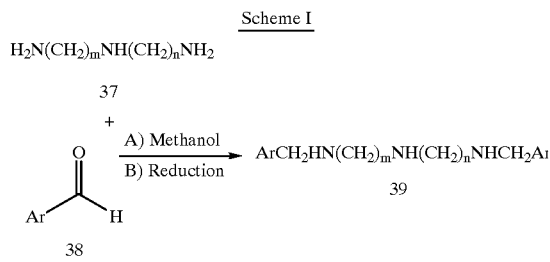

For example, in step A the appropriately substituted triamine of structure (37), such as norpermidine is treated with an excess of an appropriately substituted aldehyde of structure (38), such as benzaldehyde where Ar is phenyl in a suitable organic solvent, such as methanol in the presence of a suitable drying agent, such as 3A molecular sieves to provide the di-Schiff base. This is subsequently reduced without isolation with a suitable reducing agent, such as sodium borohydride at appropriately 0° C. to provide the desired triamine described by structure (39).

In those instances wherein R is —(CH$_2$)$_p$—Ar and p is zero such that Ar is attached directly to the terminal nitrogen atoms, then such compounds may be prepared according to the general sequence depicted in scheme J. The reagents and starting materials are readily available to one of ordinary skill in the art. All substituents unless otherwise indicated are previously defined.

Scheme J

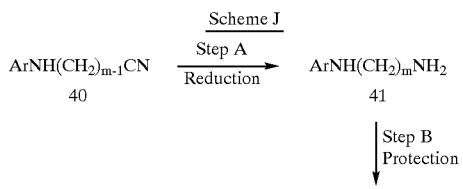

-continued

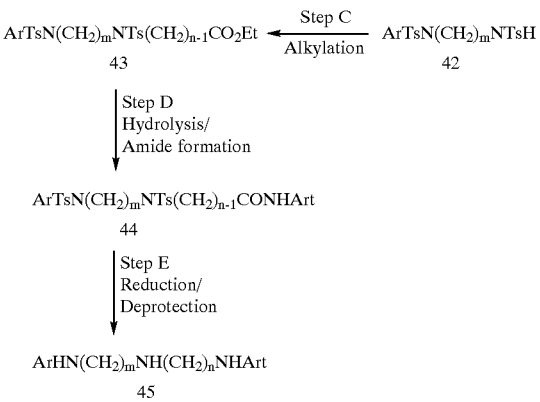

In step A, the appropriately substituted nitrile (40) is reduced to the amine of structure (41) utilizing conditions well known in the art. For example the nitrile may be reduced using lithium aluminum hydride or it can be catalytically hydrogenated.

In step B, the amine (41) is protected as the ditosylate by techniques well known in the art as previously described generally [Scheme G, step C, tri-tosylate] to provide compound (42). This is then alkylated with the appropriately substituted halo ester of formula $X(CH2)_{n-1}CO_2Et$ wherein X is chloro or bromo following generally the procedure described in scheme H, step B to provide the N-alkylated product of structure (43).

Steps D and E are followed in an analogous manner to scheme H, steps C and D wherein the primary amine utilized for the amide formation is either aniline, 1-aminonaphthalene or 2-aminonaphthalene to provide the desired triamine of structure (45).

The following examples represent typical syntheses as described by Scheme G, H, I and J. These examples are illustrative only and are not intended to limit the invention in any way. The reagents and starting materials are readily available to one or ordinary skill in the art. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor and "δ" refers to parts per million down field from tetramethylsilane.

EXAMPLE 15

$PhCH_2HN—(CH_2)_3—NH—(CH_2)_3—NHCH_2Ph$
Preparation of N-benzyl-N'-(3-benzylamino-propyl)-propane-1,3-diamine Scheme I, step A; Combine norspermidine (1.9 g, 14.3 mmol) with benzaldehyde (3.2 g, 30.0 mmol) in methanol (150 mL). Add 10 g of 3A molecular sieves and stir the reaction for 48 hours at room temperature to provide the di-Schiff base.

Scheme I, step B; Cool the above di-Schiff base solution to 0° C. and add sodium borohydride (2.2 g, 57.2 mmol) in portions. Stir for 2 hours and warm to room temperature. Filter the reaction and add water (10 mL) to the filtrate. Concentrate the filtrate under vacuum to remove the methanol and add an additional 50 mL of water. Extract the aqueous with methylene chloride (3×100 mL). Combine the organic extracts, dry over anhydrous magnesium sulfate, filter and concentrate under vacuum. Dissolve the residue in diethyl ether and treat with 2N hydrochloric acid in methanol (40 mL). Concentrate under vacuum, recrystallize the residue from methanol/water, filter and rinse the solid with acetone. Dissolve the solid in water, treat with sodium hydroxide until basic and extract the aqueous with methylene chloride (3×100 mL). Combine the organic extracts, dry over anhydrous magnesium sulfate, filter and concentrate under vacuum to provide the title compound; $^1H$ NMR (CDCl$_3$) δ 7.25–7.35 (m, 10H), 3.77 (s, 4H), 2.62–2.70 (apparent quartet, J=6 Hz, 8H), 1.65–1.75 (quintet, J=6 Hz, 4H).

EXAMPLE 16

$BuHN—(CH_2)_3—NH—(CH_2)_3—NHBu$
Preparation of N-butyl-N'-(3-butylamino-propyl)-propane-1,3-diamine Scheme G, step C; Combine norspermidine (6.55 g, 50 mmol) with 1N aqueous sodium hydroxide (200 mL) and methylene chloride (500 mL). With stirring add dropwise tosyl chloride (34.3 g, 180 mmol). Allow the reaction to stir for 2 days. Separate the layers, wash with 1N hydrogen chloride, dry over anhydrous sodium sulfate, filter and concentrate under vacuum. Purify by flash chromatography (toluene/ether, 4:1) to provide the tritosylated norspermidine (30 g) as an oil; $^1H$ NMR (CDCl$_3$) δ 7.6–7.8 (m, 8H), 7.1–7.3 (m, 6H), 3.05–3.15 (m, 4H), 2.9–3.0 (m, 4H), 2.4 (s, 9H), 1.6–1.75 (m, 4H).

Scheme G, step D; Dissolve the tritosylated norspermidine (3.6 g, 6.06 mmol) in dimethylformamide (150 mL) and treat with sodium hydride (0.53(60%) g, 13.3 mmol). After stirring for 60 minutes add butyl bromide (1.82 g, 13.3 mmol) and stir for 18 hours.

Scheme G, step E; Add aqueous 48% hydrogen bromide (70 mL) to the above tritosylated di-N-alkylated triamine (2.90 g) and heat to 100° C. under an atmosphere of nitrogen for 24 hours. After cooling concentrate the reaction under vacuum. Add isopropanol and reconcentrate. Recrystallize the residue form isopropanol/water to yield the tri-hydrobromide salt of the title compound (1.74 g) as a solid, mp>300° C.

The present invention provides a method of protecting cells from deleterious cellular effects caused by exposure to ionizing radiation or by exposure to a DNA-reactive agent.

Ionizing radiation is high energy radiation, such as an X-ray or a gamma ray, which interacts to produce ion pairs in matter. Exposure to ionizing radiation may occur as the result of environmental radiation, such as resulting from a nuclear explosion, a spill of radioactive material, close proximity to radioactive material and the like. More commonly, exposure to ionizing radiation may occur as the result of radiological medical procedures such as radiation therapy for various types of cancers.

DNA-reactive agents are those agents, such as alkylating agents, cross-linking agents, and DNA intercalating agents, which interact covalently or non-covalently with cellular DNA causing certain deleterious cellular effects. For example, DNA-reactive agents include cisplatin, cyclophosphamide, diethylnitrosoamine, benzo(a)pyrene, carboplatin, doxorubicin, mitomycin-C and the like. Many of these DNA-reactive agents, such as cisplatin, cyclophosphamide, doxorubicin and mitomycin-C are useful in cancer therapy as DNA-reactive chemotherapeutic agents.

Deleterious cellular effects caused by exposure to ionizing radiation or to a DNA-reactive agent include damage to cellular DNA, such as DNA strand break, disruption in cellular function, such as by disrupting DNA function, cell death, tumor induction, such as therapy-induced secondary tumor induction, and the like. These deleterious cellular effects can lead to secondary tumors, bone marrow suppression, kidney damage, peripheral nerve damage, gastrointestinal damage and the like. For example, in cancer radiation therapy, the exposure to radiation is intended to cause cell death in the cancer cells. Unfortunately, a large part of the adverse events associated with the therapy is caused by these deleterious cellular effects of the radiation on normal cells as opposed to cancer cells.

The present invention provides a method by which cells are protected from deleterious cellular effects by preventing or eliminating these effects or by reducing their severity. According to the present invention, the cells to be protected are contacted with a compound of formula (I) or (II) prior to or during exposure of the cell to ionizing radiation or to DNA-reactive agents. The cells may be contacted directly, such as by applying a solution of a compound of the invention to the cell or by administering a compound of the invention to a mammal. The compounds of the present invention thus provide a protective effect in the cell which eliminates or reduces the severity of the deleterious cellular effects which would otherwise be caused by the exposure.

More particularly, the present invention provides a method of protecting non-cancer, or normal, cells of a mammal from deleterious cellular effects caused by exposure of the mammal to ionizing radiation or to a DNA-reactive agent. As used herein, the term "mammal" refers to warmblooded animals such as mice, rats, dogs and humans. The compounds of the present invention provide a selective protection of normal cells, and not of cancer cells, during cancer radiation therapy and during chemotherapy with a DNA-reactive chemotherapeutic agent. According to the present invention the compound of the invention is administered to the mammal prior to or during exposure to ionizing radiation or to a DNA-reactive agent. The present invention provides a method whereby the deleterious cellular effects on non-cancer cells caused by exposure of the mammal to ionizing radiation or to a DNA-reactive agent are eliminated or reduced in severity or in extent.

In addition, the present invention provides a method of treating a patient in need of radiation therapy or in need of chemotherapy with a DNA-reactive chemotherapeutic agent. As used herein, the term "patient" refers to a mammal, including mice, rats, dogs and humans, which is afflicted with a neoplastic disease state or cancer such that it is in need of cancer radiation therapy or chemotherapy with a DNA-reactive chemotherapeutic agent. The term "neoplastic disease state" as used herein refers to an abnormal state or condition characterized by rapidly proliferating cell growth or neoplasm.

Neoplastic disease states for which treatment with a compound of formula (I) or (II) will be particularly useful in conjunction with radiation therapy or chemotherapy with a DNA-reactive chemotherapeutic agent include: Leukemias such as, but not limited to, acute lymphoblastic, acute myelogenous, chronic lymphocytic, acute myeloblastic and chronic myelocytic; Carcinomas, such as, but not limited to, those of the cervix, esophagus, stomach, pancreas, breast, ovaries, small intestines, colon and lungs; Sarcomas, such as, but not limited to, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma, Hodgkin's disease and non-Hodgkin's lymphoma. Neoplastic disease states for which treatment with a compound of formula (I) or (II) will be particularly preferred in conjunction with radiation therapy or chemotherapy include Hodgkin's disease, pancreatic carcinoma, advanced carcinoma, breast cancers, ovarian cancer, colon cancers and the like.

In addition, treatment with a compound of the present invention provides selective protection against deleterious cellular effects, such as therapy-induced secondary tumor induction, caused by radiation therapy or chemotherapy with a DNA-reactive chemotherapeutic agent. Treatment with a compound of the present invention is thus useful in eliminating or reducing the risk of secondary tumor induction, such as therapy-induced acute myelogenous leukemia and non-Hodgkin's lymphoma, brought about by radiotherapy or chemotherapy for treatment of Hodgkin's disease.

According to the present invention, administration to a patient of a compound of formula (I) or (II) prior to or during radiation therapy or chemotherapy with a DNA-reactive chemotherapeutic agent will provide a selective protection of non-cancer cells of the patient but not of cancer cells. The deleterious cellular effects on non-cancer cells caused by treatment of the patient with ionizing radiation or with a DNA-reactive chemotherapeutic agent are thus eliminated or reduced in severity or in extent.

A protective amount of a compound of formula (I) or (II) refers to that amount which is effective, upon single or multiple dose administration to a mammal or patient, in eliminating or reducing in severity or in extent the deleterious cellular effects caused by exposure to or treatment with ionizing radiation or a DNA-reactive agent. A protective amount of a compound of formula (I) or (II) also refers to that amount which is effective, upon single or multiple dose administration to the cell, in eliminating or reducing in severity or in extent the deleterious cellular effects caused by exposure to ionizing radiation or a DNA-reactive agent.

A protective amount for administration to a mammal or a patient can be readily determined by the attending diagnostician, as one skilled in the art, by the use of known techniques and by observing results obtained under analogous circumstances. In determining the protective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

The compounds of Formula (I) or (II) may be administered as single doses or as multiple doses and are ordinarily administered prior to and/or during exposure to ionizing radiation or to DNA-reactive agents. Generally, where a compound of the present invention is administered in conjunction with radiation therapy, the compound of the present invention will be administered in single or multiple doses prior to radiation therapy following a schedule calculated to provide the maximum selective protective effect during radiation therapy. Generally, where a compound of the present invention is administered in conjunction with a DNA-reactive chemotherapeutic agent, the compound of the present invention will be administered in single or multiple doses prior to and during chemotherapy following a schedule calculated to provide the maximum selective protective effect during chemotherapy.

The details of the dosing schedule for the compounds of the present invention necessary to provide the maximum selective protective effect upon exposure to ionizing radiation or to a DNA-reactive agent can be readily determined by an attending physician, as one skilled in the art, by the use of known techniques and by observing results obtained under analogous circumstances.

A protective amount of a compound of formula (I) or (II) for administration to a mammal or patient will vary from about 5 milligram per kilogram of body weight per day (mg/kg/day) to about 1000 mg/kg/day. Preferred amounts are expected to vary from about 50 to about 500 mg/kg/day.

A protective amount of a compound of formula (I) or (II) for contacting a cell will vary from about 100 micromolar to about 5 millimolar in concentration.

A compound of formula (I) or (II) can be administered to a mammal or a patient in any form or mode which makes the compound bioavailable in effective amounts, including oral and parenteral routes. For example, compounds of formula (I) and (II) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (I) or (II) in admixture or otherwise in association with one or more inert carriers. These compositions are useful, for example, as assay standards, as convenient means of making bulk shipments, or as pharmaceutical compositions. An assayable amount of a compound of formula (I) or (II) is an amount which is readily measurable by standard assay procedures and techniques as are well known and appreciated by those skilled in the art. Assayable amounts of a compound of formula (I) or (II) will generally vary from about 0.001% to about 75% of the composition by weight. Inert carriers can be any material which does not degrade or otherwise covalently react with a compound of formula (I) or (II). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (I) or (II) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel™, corn starch and the like; lubricants such as magnesium stearate or Sterotex™; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (I) or (II) in their end-use application.

Compounds of formula (I) wherein R is ethyl, propyl, butyl or —CH$_2$Ph are generally preferred. Compounds of formula (I) wherein m is 2, 3 or 4 are generally preferred. Compounds of formula (I) wherein n is 4, 7, 8 or 10 are generally preferred.

Compounds of formula (II) wherein R is propyl, butyl or —CH$_2$Ph are generally preferred. Compounds of formula (II) wherein m is 3 are generally preferred. Compounds of formula (II) wherein n is 3 are generally preferred.

The following list identifies compounds of the formula (I) or (II) which are particularly preferred embodiments of the present invention:

N,N'-Bis-(3-butylamino-propyl)-octane-1,8-diamine.4HCL;
N,N'-Bis-(3-ethylamino-propyl)-heptane-1,7-diamine.4HCl;
N,N'-Bis-(3-propylamino-propyl)-heptane-1,7-diamine-4HCl;
N,N'-Bis-(4-benzylamino-butyl)-octane-1,8-diamine.4HCL;
N,N'-Bis-(4-benzylamino-butyl)-heptane-1,7-diamine.4HCl;
N,N'-Bis-(2-benzylamino-ethyl)-octane-1,8-diamine.4HCL;
N,N'-Bis-(2-benzylamino-ethyl)-heptane-1,7-diamine.4HCl;
N,N'-Bis-(2-benzylamino-ethyl)-decane-1,10-diamine.4HCl;
N,N'-Bis-(3-benzylamino-propyl)-butane-1,4-diamine.4HCl;
N,N'-Bis-(3-benzylamino-propyl)-heptane-1,7-diamine.4HCl;
N-benzyl-N'-(3-benzylamino-propyl)-propane-1,3-diamine.HCl;
N-butyl-N'-(3-butylamino-propyl)-propane-1,3-diamine.HCl;
N-propyl-N'-(3-propylamino-propyl)-propane-1,3-diamine.HCl.

The utility of the compounds of the present invention may be demonstrated as radioprotective agents both in vitro and in vivo.

For example, the ability of cultured cells to form clones (colonies) may be evaluated as a function of exposure to X-ray dose or chemical dose. Cells are either not drug treated or are treated with a test agent 30 minutes prior to exposure. The degree of retention of ability to form clones after exposure, in comparison to untreated cells, is directly related to the protective effect of the drug. A typical experiment of this type may be carried out essentially as described by Snyder and Lachmann [*Radiation Res.* 120, 121 (1989)].

Alternatively, the production of DNA strand breaks upon exposure to X-ray dose or chemical dose may be evaluated. Cells are either not drug treated or are treated with a test agent about 30 minutes prior to exposure. The extent of DNA strand breakage after exposure, in comparison to that in untreated cells, is inversely related to the protective effect of the drug. A typical experiment of this type may be carried out essentially as described by Snyder [*Int. J. Radiat. Biol.* 55, 773 (1989)].

In addition, the survivability of mice exposed to whole body irradiation or to a DNA-reactive agent may be evaluated. Animals, either pre-treated with a test agent or untreated (Control Group), are exposed to whole body irradiation (1500 rads). Untreated control animals are expected to survive about 12–15 days. The degree of survivability of the treated animals, in comparison to the untreated controls, is directly related to the protective effect of the drug treatment. A typical experiment of this type may be carried out essentially as described by Carroll et al. [*J. Med. Chem.* 33, 2501 (1990)].

The production of DNA strand breaks in lymphocytes taken from treated animals exposed to whole body irradiation or to a DNA-reactive agent may be evaluated in comparison to untreated control. Alternatively, the viability and clonogenicity of bone marrow cells taken from treated animals exposed to whole body irradiation or to a DNA-reactive agent may be evaluated in comparison to untreated control as described by Pike and Robinson [*J. Cell Physiol.* 76, 77 (1970)].

What is claimed is:

1. A method of protecting mammalian cells from deleterious cellular effects caused by exposure to ionizing radiation comprising contacting said cells with a protective amount of a polyamine of the formula

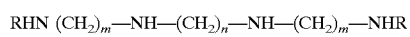

wherein m is an integer from 2 to 4 n is an integer from 3 to 10 and

R is (CH$_2$)$_p$—Ar wherein

Ar is phenyl or naphthyl and p is an integer from 0 to 2, with the proviso that when n=8 and m=3, p cannot be 1; or the pharmaceutically acceptable addition salts thereof.

2. A compound of the formula

wherein m is an integer from 2 to 4 n is an integer from 3 to 10 and

R is —Ar wherein

Ar is phenyl or naphthyl;

or the pharmaceutically acceptable addition salts thereof.

3. A compound according to claim 2 wherein m is 3 and n is 3.

4. A method of protecting mammalian cells from deleterious cellular effects caused by exposure to ionizing radiation comprising contacting said cells with a protective amount of a compound of the formula

wherein m is an integer from 2 to 4 n is an integer from 3 to 10 and

R is —(CH$_3$)$_p$ Ar wherein

Ar is phenyl or naphthyl and p is an integer from 0 to 2;

or the pharmaceutically acceptable addition salts thereof.

5. A method of protecting mammalian cells from deleterious cellular effects caused by exposure to a DNA-reactive agent comprising contacting said cells with a protective amount of a polyamine of the formula

wherein m is an integer from 2 to 4 n is an integer from 3 to 10 and

R is —(CH$_2$)$_p$—Ar wherein

Ar is phenyl or naphthyl and p is an integer from 0 to 2, with the proviso that when n=8 and m=3, p cannot be 1;

or the pharmaceutically acceptable addition salts thereof.

6. A method of protecting mammalian cells from deleterious cellular effects caused by exposure to a DNA-reactive agent comprising contacting said cells with a protective amount of a compound of the formula

RHN—(CH$_2$)$_m$—NH—(CH$_2$)$_n$ NHR wherein m is an integer from 2 to 4 n is an integer from 3 to 10 and

R is —(CH$_2$)$_p$ Ar wherein

Ar is phenyl or naphthyl, p is an integer from 0 to 2;

or the pharmaceutically acceptable addition salts thereof.

7. A method of protecting non-cancer cells of a human from deleterious cellular effects caused by exposure to ionizing radiation comprising administering to said human a protective amount of a polyamine of the formula

RHN—(CH$_2$)$_m$—NH—(CH$_2$)$_n$—NH—(CH$_2$)$_m$—NHR wherein m is an integer from 2 to 4 n is an integer from 3 to 10 and

R is —(CH$_2$)$_p$—Ar wherein

Ar is phenyl or naphthyl and p is an integer from 0 to 2, with the proviso that when n=8 and m=3, p cannot be 1;

or the pharmaceutically acceptable addition salts thereof.

8. A method of protecting non-cancer cells of a human from deleterious cellular effects caused by exposure to ionizing radiation comprising administering to said human a protective amount of a compound of the formula

RHN—(CH$_2$)$_m$—NH—(CH$_2$)$_n$—NHR wherein m is an integer from 2 to 4 n is an integer from 3 to 10 and

R is (CH$_2$)$_p$ Ar wherein

Ar is phenyl or naphthyl, p is an integer from 0 to 2;

or the pharmaceutically acceptable addition salts thereof.

9. A method of protecting non-cancer cells of a human from deleterious cellular effects caused by exposure to a DNA-reactive agent comprising administering to said human a protective amount of a polyamine of the formula

RHN—(CH$_2$)$_m$—NH—(CH$_2$)$_n$—NH—(CH$_2$)$_m$—NHR wherein m is an integer from 2 to 4 n is an integer from 3 to 10 and

R is —(CH$_2$)$_p$—Ar wherein

Ar is phenyl or naphthyl and p is an integer from 0 to 2, with the proviso that when n=8 and m=3, p cannot be 1;

or the pharmaceutically acceptable addition salts thereof.

10. A method of protecting non-cancer cells of a human from deleterious cellular effects caused by exposure to a DNA-reactive agent comprising administering to said human a protective amount of a compound of the formula

RHN—(CH$_2$)$_m$—NH—(CH$_2$)$_n$—NHR wherein m is an integer from 2 to 4 n is an integer from 3 to 10 and

R is —(CH$_2$)$_p$—Ar wherein

Ar is phenyl or naphthyl, p is an integer from 0 to 2;

or the pharmaceutically acceptable addition salts thereof.

11. A method of treating a patient in need of radiation therapy comprising administering to said patient a protective amount of a polyamine of the formula

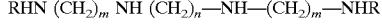

RHN (CH$_2$)$_m$ NH (CH$_2$)$_n$—NH—(CH$_2$)$_m$—NHR wherein m is an integer from 2 to 4 n is an integer from 3 to 10 and

R is —(CH$_2$)$_p$—Ar wherein

Ar is phenyl or naphthyl and p is an integer from 0 to 2, with the proviso that when n=8 and m=3, p cannot be 1;

or the pharmaceutically acceptable addition salts thereof.

12. A method of treating a patient in need of radiation therapy comprising administering to said patient a protective amount of a compound of the formula

RHN—(CH$_2$)$_m$—NH—(CH$_2$)$_n$—NHR wherein m is an integer from 2 to 4 n is an integer from 3 to 10 and

R is —(CH$_2$)$_p$—Ar wherein

Ar is phenyl or naphthyl, p is an integer from 0 to 2;

or the pharmaceutically acceptable addition salts thereof.

13. A method of treating a patient in need of chemotherapy with a DNA-reactive chemotherapeutic agent comprising administering to said patient a protective amount of a polyamine of the formula

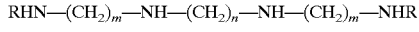

RHN—(CH$_2$)$_m$—NH—(CH$_2$)$_n$—NH—(CH$_2$)$_m$—NHR wherein m is an integer from 2 to 4 n is an integer from 3 to 10 and

R is —(CH$_2$)$_p$—Ar wherein
  Ar is phenyl or naphthyl and
  p is an integer from 0 to 2,
with the proviso that when n=8 and m=3, p cannot be 1; or the pharmaceutically acceptable addition salts thereof.

14. A method of treating a patient in need of chemotherapy with a DNA-reactive chemotherapeutic agent comprising administering to said patient a protective amount of a compound of the formula

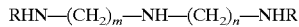

wherein
  m is an integer from 2 to 4
  n is an integer from 3 to 10 and
  R is —$(CH_2)_p$—Ar
  wherein
    Ar is phenyl or naphthyl,
    p is an integer from 0 to 2;
or the pharmaceutically acceptable addition salts thereof.

15. A pharmaceutical composition comprising a protective amount of a compound of the formula

wherein
  m is an integer from 2 to 4
  n is an integer from 3 to 10 and
  R is —Ar
  wherein
    Ar is phenyl or naphthyl;
or the pharmaceutically acceptable salts thereof.

* * * * *